US005627055A

United States Patent [19]
Goodchild et al.

[11] Patent Number: 5,627,055
[45] Date of Patent: May 6, 1997

[54] FINDERONS AND METHODS OF THEIR PREPARATION AND USE

[75] Inventors: John Goodchild, Westborough; Thomas E. Leonard, Marlboro, both of Mass.

[73] Assignee: Hybridon, Inc., Worcester, Mass.

[21] Appl. No.: 475,867

[22] Filed: Jun. 7, 1995

Related U.S. Application Data

[62] Division of Ser. No. 315,287, Sep. 29, 1994.

[51] Int. Cl.$^6$ .......................... C12P 19/34; C07H 21/02; C07H 21/04
[52] U.S. Cl. ........................ 435/91.31; 536/231
[58] Field of Search ..................... 435/91.1, 199, 435/6, 91.31, 172.1, 172.3; 536/25.3, 23.1, 24.5

[56] References Cited

U.S. PATENT DOCUMENTS

| 4,987,071 | 1/1991 | Cech et al. | 435/91.31 |
| 5,144,019 | 9/1992 | Rossi et al. | 536/23.1 |

FOREIGN PATENT DOCUMENTS

| WO92/07065 | 4/1992 | WIPO . |
| WO93/15187 | 8/1993 | WIPO . |
| WO93/15194 | 8/1993 | WIPO . |
| WO94/03596 | 2/1994 | WIPO . |
| WO94/10301 | 5/1994 | WIPO . |
| WO94/12633 | 6/1994 | WIPO . |

OTHER PUBLICATIONS

Morrow Adv. Inorg. Biochem 9 41–74 (1994) Artificial Ribonucleases.
Buzayan et al. (1990) *Nuc. Acids Res.* 18:4447–4451.
Dahm et al. (1990) *Biochimie* 72:819–23.
Odai et al. (1990) *FEBS Lett.* 267:150–152.
Perreault et al. (1990) *Nature* 344:565–567.
Ruffner et al. (1990) *Nucleic Acids Res.* 18:6025–6029.
Goodchild et al. (1991) *Arch. Biochem. Biophys.* 284:386–391.
Koizumi et al. (1991) *Biochem.* 30:5145–5150.
Olsen et al. (1991) *Biochem.* 30:9735–9741.
Perreault et al. (1991) *Biochem.* 30:4020–4025.
Pieken et al. (1991) *Science* 253:314–317.
McCall et al. (1992) *Proc. Natl. Acad. Sci. (USA)* 89:5710–5714.
Benseler et al. (1993) *J. Am. Chem. Soc.* 115:8483–8484.
Ma et al. (1993) *Nucleic Acids Res.* 21:2585–2589.
Ma (1993) *Biochem.* 32:1751–1758.
Thomson et al. (1993) *Nucleic Acids Res.* 21:5600–5603.
Tuschl et al. (1993) *Proc. Natl. Acad. Sci. (USA)* 90:6991–6994.
Dong–jing Fu et al. (1994) *J. Am. Chem. Soc.* (1994) 116:4591–4598.
Hendry et al. (1994) *Biochimica et Biophysica Acta* 1219:405–412.
Nesbitt et al. (1994) *Antisense Research and Development* 4:243–249.
Goodchild (1992) *Nucleic Acids Research* 20:4607–4612.

*Primary Examiner*—James Ketter
*Assistant Examiner*—John S. Brusca
*Attorney, Agent, or Firm*—Hale and Dorr

[57] ABSTRACT

Disclosed is a finderon having the ability to endonucleolytically cleave a sequence of 3' to 5' linked ribonucleotides. The finderon includes a rigid linker comprising at least one non-nucleotidic unit, flanked by first and second flanking regions of at least four contiguous, covalently-linked nucleotides. At least a portion of each flanking region is complementary to a target region on a substrate RNA molecule. Also disclosed are methods of preparing and using a finderon, and kits including a finderon.

15 Claims, 6 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA/RNA ( i i i ) HYPOTHETICAL: NO ( i v ) ANTI-SENSE: YES ( x i ) SEQUENCE DESCRIPTION: SEQ ID NO:1:

TTTCCACACT NNNNACTAAA AGGG    24

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA/RNA ( i i i ) HYPOTHETICAL: NO ( i v ) ANTI-SENSE: YES ( x i ) SEQUENCE DESCRIPTION: SEQ ID NO:2:

TTTCCACACT NNNNNNNNAC TAAAAGGG    28

( 2 ) INFORMATION FOR SEQ ID NO:3:

( i ) SEQUENCE CHARACTERISTICS:

(A) LENGTH: 32 base pairs
                (B) TYPE: nucleic acid
                (C) STRANDEDNESS: single
                (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:3:

TTTCCACACT NNNNNNNNN NNACTAAAAG GG					32

(2) INFORMATION FOR SEQ ID NO:4:

(i) SEQUENCE CHARACTERISTICS:
                (A) LENGTH: 16 base pairs
                (B) TYPE: nucleic acid
                (C) STRANDEDNESS: single
                (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:4:

CACACTNNNN ACTAAA					16

(2) INFORMATION FOR SEQ ID NO:5:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:5:

CACACTNNNN NNNNACTAAA					20

(2) INFORMATION FOR SEQ ID NO:6:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:6:

CACACTNNNN NNNNNNNNAC TAAA					24

(2) INFORMATION FOR SEQ ID NO:7:

(i) SEQUENCE CHARACTERISTICS:
                (A) LENGTH: 9 base pairs
                (B) TYPE: nucleic acid
                (C) STRANDEDNESS: single
                (D) TOPOLOGY: linear (i i) MOLECULE TYPE: cDNA/RNA (i i i) HYPOTHETICAL: NO (i v) ANTI-SENSE: YES (x i) SEQUENCE DESCRIPTION: SEQ ID NO:7:

CACTNACTA                                                                                          9

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: cDNA/RNA (i i i) HYPOTHETICAL: NO (i v) ANTI-SENSE: YES (x i) SEQUENCE DESCRIPTION: SEQ ID NO:8:

CACTNNNNAC TA                                                                                    12

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: cDNA/RNA (i i i) HYPOTHETICAL: NO (i v) ANTI-SENSE: YES (x i) SEQUENCE DESCRIPTION: SEQ ID NO:9:

CACTNNNNNN ACTA                                                                                 14

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: cDNA/RNA (i i i) HYPOTHETICAL: NO (i v) ANTI-SENSE: YES (x i) SEQUENCE DESCRIPTION: SEQ ID NO:10:

CCGAACGGCG GTTTCNNNNA CTAAATCGAA GCAT                                    34

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: cDNA/RNA (i i i) HYPOTHETICAL: NO ( i v ) ANTI-SENSE: YES ( x i ) SEQUENCE DESCRIPTION: SEQ ID NO:11:

CCGAACGGCG GTTTCNNNNN NNNACTAAAT CGAAGCAT 38

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA/RNA ( i i i ) HYPOTHETICAL: NO ( i v ) ANTI-SENSE: YES ( x i ) SEQUENCE DESCRIPTION: SEQ ID NO:12:

CCGAACGGCG GTTTCNNNNN NNNNNNNAC TAAATCGAAGC AT 42

( 2 ) INFORMATION FOR SEQ ID NO:13:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: YES ( x i ) SEQUENCE DESCRIPTION: SEQ ID NO:13:

GGGAUUUUCC ACACUCUGAU GAGGCCGUUA GGCCGAAACU AAAAGUU 47

( 2 ) INFORMATION FOR SEQ ID NO:14:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:14:

AGGGTCTGTT TTC 13

( 2 ) INFORMATION FOR SEQ ID NO:15:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: YES ( x i ) SEQUENCE DESCRIPTION: SEQ ID NO:15:

| | |
|---|---|
| GGGAAAACAG ACCCUUUUAG UCAGUGUGGA AAAUC | 3 5 |

( 2 ) INFORMATION FOR SEQ ID NO:16:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: YES ( x i ) SEQUENCE DESCRIPTION: SEQ ID NO:16:

| | |
|---|---|
| CACACUCUGA UGAGGCCGUU AGGCCGAAAC U | 3 1 |

FINDERONS AND METHODS OF THEIR PREPARATION AND USE

CROSS-REFERENCE TO RELATED APPLICATION

This is a divisional application of patent application Ser. No. 08/315,287, entitled "FINDERONS AND METHODS OF THEIR PREPARATION AND USE", filed on Sep. 29, 1994, assigned to the present assignees, and is related to patent application Ser. Nos. 08/477,883 and 08/472,427, both entitled "FINDERONS AND METHODS OF THEIR PREPARATION AND USE", both filed on Jun. 7, 1995, and both assigned to the present assignees.

BACKGROUND OF THE INVENTION

This invention relates to novel molecules called finderons useful with endonucleolytic activity and enhanced half-lives useful in the site-specific cleavage of RNA. This invention also relates to the control of gene expression through the degradation of mRNA.

Ribozymes are RNA molecules with catalytic activities including the ability to cleave at specific phosphodiester linkages in RNA molecules to which they have hybridized, such as mRNAs, RNA-containing substrates, and ribozymes, themselves.

Ribozymes may assume one of several physical structures, one of which is called a "hammerhead". A hammerhead ribozyme is composed of a catalytic core containing nine conserved bases, a double-stranded stem and loop structure (stem-loop II), and two regions complementary to the target RNA flanking the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3', 5'-phosphate diester to a 2', 3'-cyclic phosphate diester. It is currently believed that this catalytic activity requires the presence of specific, highly conserved sequences in the catalytic region of the ribozyme.

Although the endonucleolytic activity of ribozymes has been demonstrated in vitro, their use in vivo has been limited by their susceptibility to RNAses. Furthermore, therapeutics such as ribozymes having greater than 30 or more nucleotides are more expensive and difficult to produce in great quantities. Thus, there is a need for smaller molecules with increased nuclease resistance that can be used to cleave RNA in vitro and in vivo, and to control gene expression for in vivo use.

In an effort to protect antisense oligonucleotides from degradative influences in vivo, various structural modifications have been made to these molecules, including the replacement of phosphodiester linkages with non-phosphodiester linkages, the substitution of various sugar groups and bases, the addition of end-capping groups, and the substitution or replacement of existing structures with the self-hybridizing termini (reviewed in Goodchild (1990) *Biocougate Chemist* 2:165–187; Agrawal et al. (1992) *Tren Biotechnol.* 10:152–158; and see WO 94/10301; WO 93/15194; WO 94/12633).

However, modifications which protect an RNA molecule from endonuclease digestion may also affect the catalytic activity of the ribozyme. For example, Perreault et al. (*Nature* (1990) 344:565–567) report that the replacement of ribonucleotides at various conserved positions within the ribozyme sequence with 2'-deoxynucleotides resulted in a 96% decrease of catalytic efficiency. Perreault et al. (*Biochem.* (1991) 30:4020–4025) and Dahn et al. (*Biochem.* (1990) 72:819–23) disclose that the replacement of various 2'-hydroxyl groups with hydrogen atoms reduced the catalytic activity of hammerhead ribozymes. Olsen et al. (*Biochem.* (1991) 30:9735–9741) report that replacing 2'-hydroxyl groups on all adenosine residues by either fluorine or hydrogen decreases the catalytic activity of a ribozyme. Odai et al. (*FEBS Lett.* (1990) 267:150–152) report that replacing the exocyclic amino group of a conserved guanosine residue in the core region with hydrogen reduced catalytic activity. Ruffner et al. (*Nucleic Acids Res.* (1990) 18:6025–6029) and Buzayan et al. (*Nuc. Acids Res.* (1990) 18:4447–4451) disclose that replacing oxygen atoms by sulfur on various internucleotide phosphate residues reduces catalytic activity. Pieken et al. (*Science* (1991) 253:314–317) disclose that catalytic activity is reduced when various 2'-hydroxyl groups on adenosine residues are replaced with fluorine and when the 2'-hydroxyl groups on cytidine residues is replaced with amine groups.

Other groups have substituted nucleotides within the ribozyme with nucleotide analogs. For example, Usman et al. (WO 93/15187) designed chimeric polymers or "nucleozymes" with ribozyme-like catalytic activity having ribonucleotides or nucleic acid analogs (with modified sugar, phosphate, or base) at catalytically critical sites and nucleic acid analogs or deoxyribonucleotides at non-catalytically critical sites.

Recently, modifications such as a reduction in the length of the stem-loop II structure of the hammerhead ribozyme have been made in an effort to design a more stable molecule without reducing its catalytic activity.

For example, Goodchild et al. (*Arch. Biochem. Biophys.* (1991) 284:386–391) replaced stem II and loop II with shorter nucleotide sequences. Tuschl et al. (*Proc. Natl. Acad. Sci. (USA)* (1993) 90:6991–6994) prepared hammerhead ribozymes with the stem II shortened to two base pairs, closed by a four base-pair loop. McCall et al. (*Proc. Natl. Acad. Sci. (USA)* 89:5710–5714) replaced the stem-loop with a few nucleotides that cannot form Watson-Crick base pairs between themselves, and/or substituted the stem-loop II and flanking arms with DNA, without reducing activity.

Modifications in ribozyme structure have also included the substitution or replacement of various non-catalytic core portions of the molecule with non-nucleotidic molecules. For example, Benseler et al. (*J. Am. Chem. Soc.* (1993) 115:8483–8484) disclosed hammerhead-like molecules in which two of the base pairs of stem II, and all four of the nucleotides of loop II were replaced with non-nucleoside linkers based on hexaethylene glycol, propanediol, bis (triethylene glycol) phosphate, tris (propanediol) bisphosphate, or bis (propanediol) phosphate. Ma et al. (*Biochem.* (1993) 32:1751–1758; *Nucleic Acids Res.* (1993) 21:2585–2589) replaced the six nucleotide loop of the TAR ribozyme hairpin with non-nucleotidic, ethylene glycol-related linkers. Thomson et al. (*Nucleic Acids Res.* (1993) 21:5600–5603) replaced loop II with linear, non-nucleotidic linkers of 13, 17, and 19 atoms in length.

However, the entire catalytic core of the ribozymes has heretofore not been replaced with non-nucleotidic molecules without affecting the ability of the molecule to cleave RNA. Thus what is needed are smaller catalytic molecules with increased nuclease resistance that are capable of endonucleolytically cleaving single-stranded RNA, and which can be quickly and cost-effectively prepared.

SUMMARY OF THE INVENTION

The present invention provides catalytic molecules with increased nuclease resistance that are capable of endonucleolytically cleaving single-stranded RNA. These catalytic molecules or "finderons" include a rigid, non-nucleotidic linker comprising at least one molecule of "unit" which is responsible for the catalytic activity of the molecule.

It has been discovered that replacement of the entire catalytic core and stem-loop II regions of a ribozyme with at least one rigid, non-nucleotidic molecule can be accomplished without extinguishing the ability of the resulting structure to endonucleolytically cleave single-stranded RNA. Although ribozymes with nucleotidic and non-nucleotidic substitutions have previously been prepared, none have included extensive substitutions in the conserved regions of the catalytic core and maintained their ability to endonucleolytically cleave single-stranded RNA, lending support to the currently accepted belief that a specific conserved nucleotide sequence is required for activity. In addition, none of the substituted ribozymes to date have contained rigid, non-nucleotidic molecules such as those set forth in this application.

These findings have been exploited to develop the present invention which, in one aspect, includes "finderons," or molecules with the ability to endonucleolytically cleave a sequence of 3' to 5' covalently-linked ribonucleotides. The finderons of the invention include a rigid molecular linker comprising at least one nonnucleotidic molecule or "unit" which, in some preferred embodiments, includes a cyclohexane diol, steroid, lupene diol, or isosorbide.

For purposes of the invention described herein, the term "rigid" refers to the physical state of molecular structures having degrees of freedom of intramolecular rotation that are restricted in comparison with those of a simple linear chain.

The term "non-nucleotidic" is used herein to describe molecules or specific portions thereof which do not include nucleotides or nucleotide analogs. Accordingly, the term "nucleotidic" refers to nucleotide- or nucleotide analog-containing molecules or specific portions thereof.

The linker is flanked by, and covalently linked to, first and second flanking regions which each comprise at least four contiguous, covalently-linked nucleotides. The first flanking region is covalently linked via its 3' terminus to the linker, and the second flanking region is covalently linked via its 5' terminus to the linker. At least portions of the first and second flanking regions are complementary to first and second target regions, respectively, on an RNA molecule to be cleaved. As used herein, the term "complementary" refers to the ability of the flanking region to hybridize with a specific sequence of nucleotides in the normal Watson-Crick base-pairing fashion. Preferably, such hybridization occurs under physiological conditions of salt and temperature, i.e., at about 140 mM NaCl and 37° C.

In some embodiments, the rigid linker in the finderon establishes a linear distance of about 15 to 30 Angstroms (equivalent to 3–5 cyclohexane diol units) between the first and second flanking regions.

In preferred embodiments, the linker establishes a conformation in the substrate RNA at the point of cleavage that resembles the trigonal, bipyramidal transition state for the cleavage reaction in which the 2' and 5' oxygen atoms attached to the phosphorous are in line. This requires that the zeta angle, or the angle of rotation about the bond between the 3' oxygen and the phosphorus atom at the cleavage site is about 180 degrees.

In embodiments wherein the linker consists of greater than one non-nucleotidic molecule, these molecules are covalently-linked via a phosphodiester, alkylphosphonate, phosphorothioate, phosphorodithioate, alkylphosphonothioate, phosphoramidate, phosphate triester, carbamate, carbonate, acetamidate, or carboxymethyl ester linkage, or by a combination thereof if greater than two non-nucleotidic molecules comprise the linker.

In some embodiments of the invention, the linker includes at least one cyclohexane diol unit. In some preferred embodiments, this linker includes at least four, and preferably four to twenty contiguous, covalently-linked cyclohexane diol units, such as trans-1,2-cyclohexane diols, cis-1,2-cyclohexane diols, trans-1,3-cyclohexane diols, cis-1,3-cyclohexane diols, trans-1,4-cyclohexane diols, cis-1,4-cyclohexane diols, or combinations thereof. One specific finderon of the invention has a linker consisting of four cyclohexane diol units.

In some embodiments, the first and second flanking regions to which the linker is attached each include at least 6 to 15 covalently-linked nucleotides. These nucleotides are deoxyribonucleotides, analogs of deoxyribonucleotides, ribonucleotides, analogs of ribonucleotides, or combinations thereof. One specific finderon of the invention includes at least one ribonucleotide, such as adenosine, in its first flanking region.

As used herein, the terms "nucleotide analog", "deoxyribonucleotide analog", and "ribonucleotide analog" are meant to encompass a nucleotide having a modified structure. Modifications include additions to, reductions in, or substitutions in any portion of the nucleotide include its sugar, base, or side groups.

In some embodiments, the ribonucleotide or deoxyribonucleotide analogs are alkylphosphonates, phosphorothioates, phosphorodithioates, alkylphosphonothioates, phosphoramidates, phosphate esters, phosphate triesters, carbamates, carbonates, acetamidates, carboxymethyl esters, or combinations thereof. One particular ribonucleotide analog is a 2'-O-alkyl ribonucleotide analog, most preferably, a methyl ribonucleotide analog. In preferred embodiments, these nucleotides and their analogs are covalently linked via an internucleotide linkage selected from the group consisting of a phosphodiester, alkylphosphonate, phosphorothioate, phosphorodithioate, phosphate triester, alkylphosphonothioate, phosphoramidate, carbamate, carbonates, acetamidates, carboxymethyl ester linkage, or a combination thereof.

In another aspect, the invention provides a method of controlling the expression of a single-stranded RNA. In this method, a finderon is provided and used to contact the RNA. Once hybridized to the RNA, the finderon cleaves it, thereby controlling its expression. In some embodiments of the method, the RNA to be cleaved is also contacted with a facilitator oligonucleotide at the same time as the RNA is contacted with the finderon. Contact with the facilitator molecule appears to enhance the endoribonucleolytic activity of the finderon.

As used herein, a "facilitator oligonucleotide" encompasses oligonucleotides which are complementary and hybridizable to a sequence of ribonucleotides making up the RNA substrate which is adjacent to a nucleotide sequence targeted by either flanking region of the finderon, and which enhances the cleavage activity of the finderon.

In another aspect of the invention, a method of site-specifically cleaving a single-stranded, RNA-containing substrate is provided which includes contacting the RNA-containing molecule with a finderon for a time sufficient for the finderon to hybridize to and cleave the RNA substrate. The term "site-specifically cleaving" refers to enzymatically cutting the substrate RNA molecule at a site before or after a particular sequence of ribonucleotides. In some embodiments, the method further includes contacting the RNA substrate with a facilitator oligonucleotide at the time it is contacted with the finderon.

The invention further provides kits useful for carrying out the method of site-specifically cleaving single-stranded RNA substrates or other methods of the invention, or, along with an RNA ligase, for preparing recombinant RNA molecules. The kit includes a container including at least one finderon of the invention, and in some embodiments, it further includes a facilitator oligonucleotide or an RNA ligase.

Another aspect of the invention is a method of preparing a finderon. In one embodiment of this method, a first flanking region is formed by covalently linking together a plurality of nucleotides. This is accomplished by linking the 3' terminus of one nucleotide to the 5' end of another nucleotide, and so on. Then, at least one non-nucleotidic molecule is attached to the 3' end of the first flanking region via a covalent linkage selected from the group consisting of phosphodiesters, alkylphosphonates, phosphorothioates, phosphorodithioates, alkylphosphonothioates, phosphoramidates, phosphate esters, carbamates, carbonates, acetamidates, and carboxymethyl esters linkage. Additional non-nucleotidic molecules may be covalently bound, one by one, to each other. The non-nucleotidic molecule or molecules form the rigid molecular linker.

Alternatively, a linker having a first and a second end can be preassembled from its component non-nucleotidic molecules and covalently linked via its first end to the 3'-terminus of the first flanking region and via its second end to the 5'-terminus of the second flanking region. A second nucleotidic flanking region is then built onto the second end of the linker. This is accomplished by linking the 3' terminus of a nucleotide to a terminal non-nucleotidic molecule of the linker, followed by the covalent linkage of a plurality nucleotides, one at a time, to the nucleotide already bound to the linker, and then to each other; the 3' terminus of the nucleotide to be bound linked to the 5' terminus of the nucleotide already bound, thereby forming a second flanking region linked to the linker.

Alternatively, the first flanking region, the second flanking region, and the non-nucleotidic linker can be synthesized separately and then covalently linked together such that the 3' terminus of the first flanking region is linked to the first end of the linker, and the 5' terminus of the second flanking is linked to the second end of the linker.

Another aspect of the invention is a finderon prepared according to the method described above. Yet another aspect is a therapeutic formulation including a finderon of the invention in a physiologically acceptable carrier.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

The patent and scientific literature referred to herein establishes the knowledge that is available to those with skill in the art. The issued U.S. patent, allowed patent applications, and articles cited herein are hereby incorporated by reference.

Figure 1:
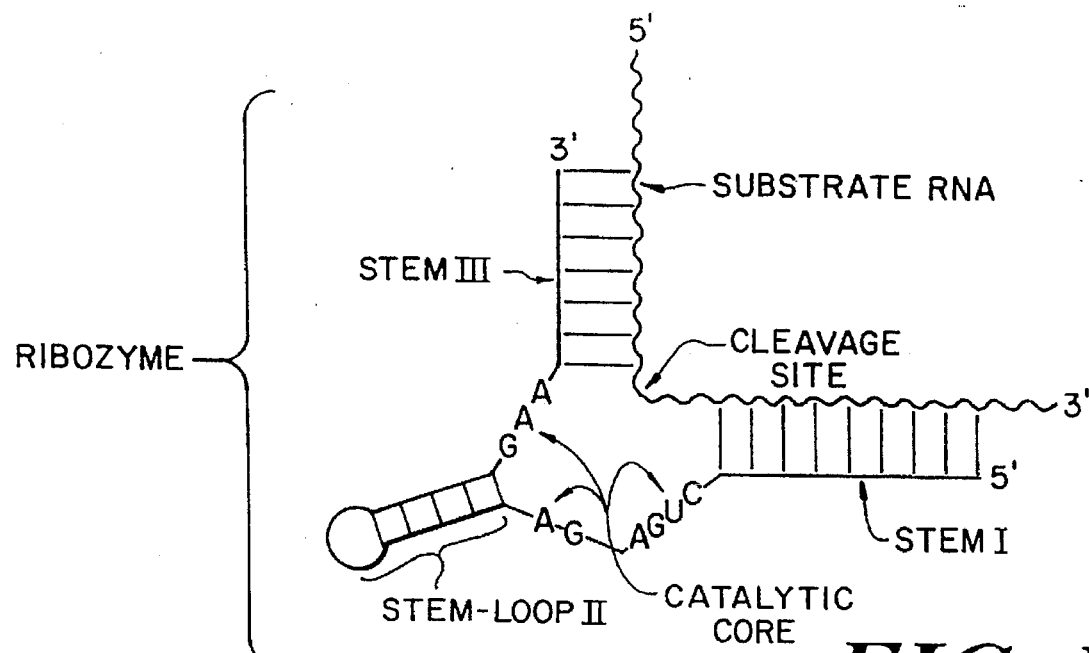
FIG. 1 is a diagrammatic representation of a consensus hammerhead ribozyme hybridized with a substrate RNA, wherein the conserved nucleotides in the catalytic core are indicated.

The hammerhead ribozyme, as engineered by Haseloff and Gerlach (*Nature* (1988) 334:585–591) and as depicted in FIG. 1, is composed of a double-stranded stem and loop structure (stem-loop II) connecting two portions of acatalytic core having nine conserved ribonucleotides, and flanked by two regions complementary to the target RNA. The flanking regions enable the ribozyme to bind to the target RNA specifically by forming double stranded stems I and III. Although current belief is that the nucleotide sequence of the ribozymal catalytic core region must be largely conserved in order to maintain the ability of the ribozyme to cleave single-stranded RNA (Koizumi et al. (1991) *Biochem.* 30:5145–5150; Thomson et al. (1993) *Nucleic Aci Res.* 21:5600–5603), it has now been discovered that this cleavage can be accomplished with molecules having catalytic regions containing neither nucleotides nor nucleotide analogs, but rather containing rigid, non-nucleotidic molecules.

These findings have been exploited to develop the present invention, which provides catalytic molecules or "finderons" which contain a rigid, non-nucleotidic linker having the ability to endonucleolytically cleave single-stranded RNA and RNA-containing substrates.

Figure 2:
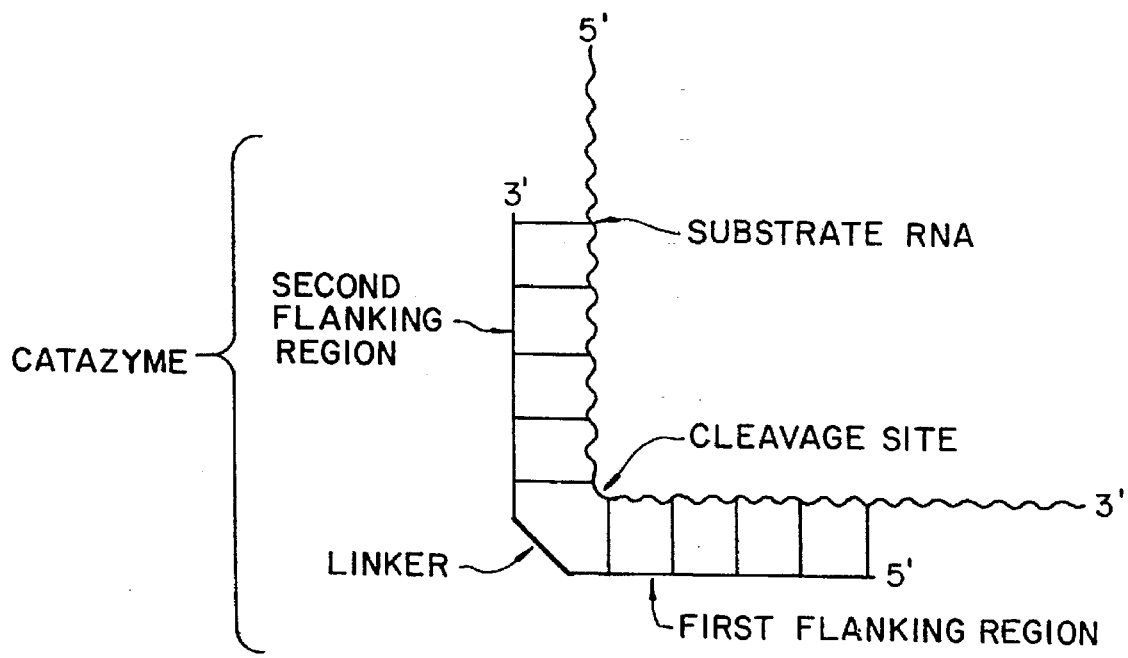
FIG. 2 is a diagrammatic representation of a finderon of the present invention hybridized with substrate RNA.

The finderons of the invention are structurally distinct from a hammerhead ribozyme in that the catalytic core of the ribozyme has been entirely replaced with an enzymatically active molecular linker that contains neither nucleotides nor nucleotide analogs, as depicted in FIG. 2. The linker is rigid and contains at least one non-nucleotidic molecule or "unit" which may be a cyclohexane diol, steroid, lupene diol, and isosorbide, or a combination thereof when the linker consists of more than one molecule. A representative cyclohexane diol, isosorbide, steroid, and lupene diol are shown in FIGS. 3A–3D, respectively.

Figure 8:
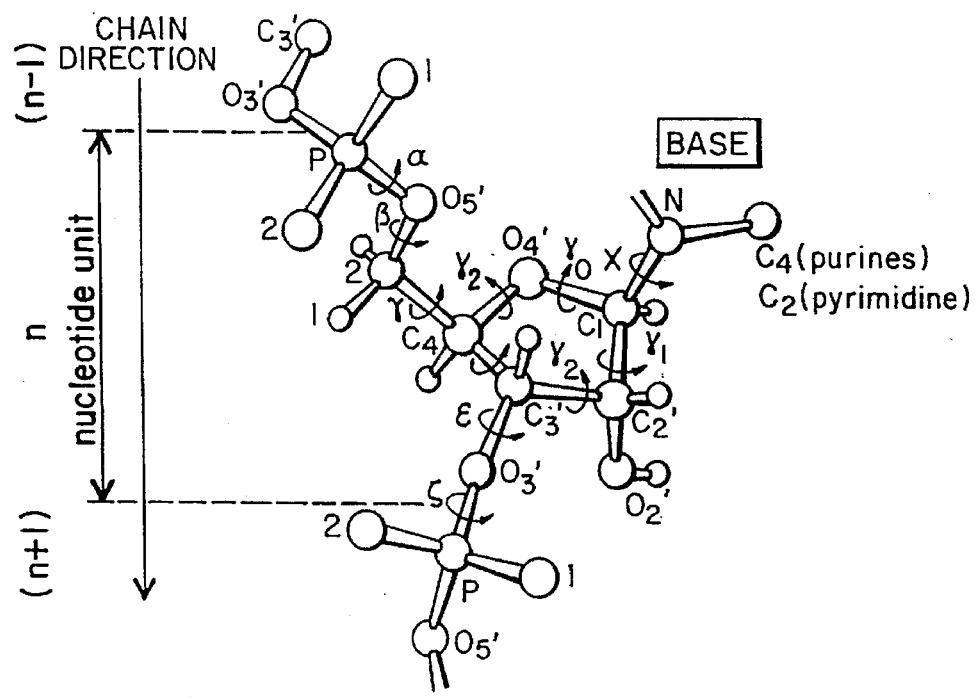
FIG. 8 is a schematic representation of the zeta angle of an oligonucleotide.

The rigidity of the molecule(s) making up the linker aids in maintaining the catalytic activity of the finderon. The linker establishes a conformation in the substrate RNA at the point of cleavage that resembles the trigonal bipyramidal transition state for the cleavage reaction in which the 2' and 5' oxygen atoms attached to the phosphorus atom are in line. This requires that the "zeta angle", or the angle of rotation about the bond between the 3' oxygen and the phosphorus atom at the cleavage site be about 180 degrees (see FIG. 8 taken from Saenger, (1983) *Principles of Nucleic Acid Structure*, Springer-Verlag, N.Y.).

The molecular linker may be prepared from various commercially available (e.g., from the Alrich Chemical Co., Milwaukee, Wis.) non-nucleotidic units such as cyclohexane diols, lupene diols, steroids such as β-estradiols, and isosorbide. The precursor molecule is then derivatized in the same way as nucleotides are derivatized for automated synthesis (e.g., dimethoxytritylation and phosphytylation). Alternatively, the non-nucleotidic molecule is synthesized from more basic starting components using methodologies known in the art or by new protocols, such as those as described in the exemplification below.

Figure 4:
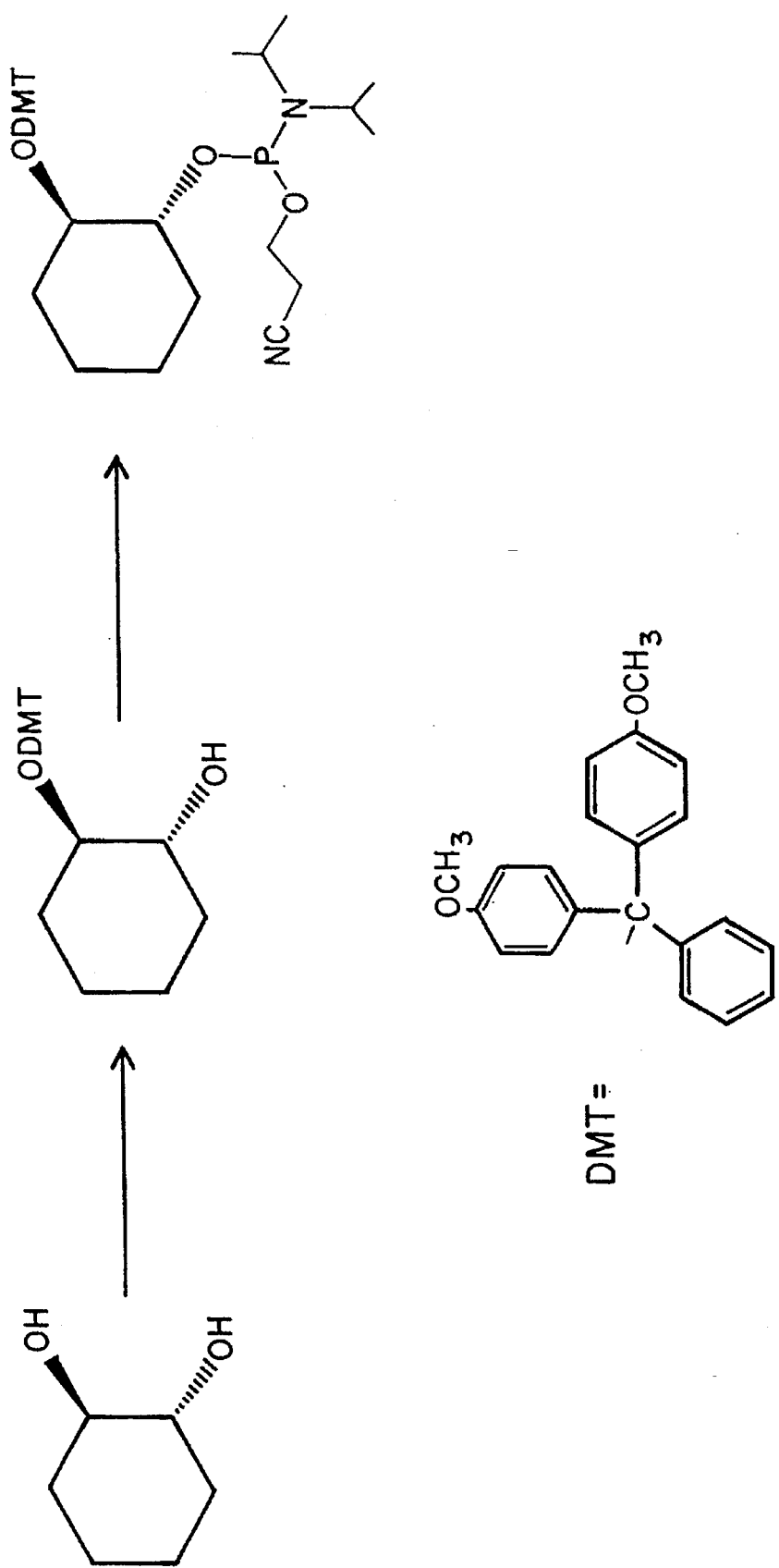
FIG. 4 is a diagrammatic representation of the preparation of a cyclohexane diol unit useful in the molecular linker of a finderon.

For example, the cyclohexane diol unit trans-1-O-(4,4'-dimethoxytrityl)-2-O-[β-cyanoethoxy- (N,N-diisopropylamino)]phosphino-1, 2-cyclohexanediol (FIG. 3A) can be prepared from trans-1-O-dimethoxytrityl cyclohexane diol which itself is prepared from trans-1,2-cyclohexane diol by treatment with dimethoxytrityl chloride and dimethylaminopyridine. This synthesis is depicted in FIG. 4. The precursor so prepared is dried by evaporation of tetrahydrofuran (THF) dissolved in THF and diisopropylethylamine, treated with β-cyanoethyoxy-N,N-diisopropylaminochlorophosphine, and chromatographed on a silica gel column.

Figure 3A:
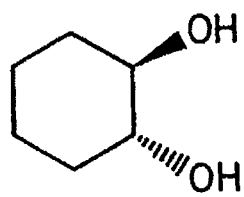
FIG. 3A is a diagrammatic representation of a representative cyclohexane diol unit useful in the molecular linker of the finderon.
Figure 3B:
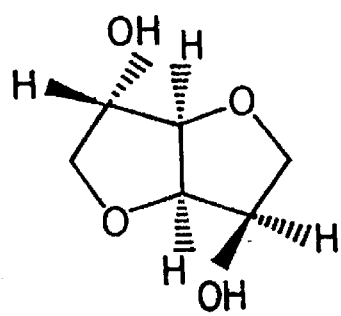
FIG. 3B is a diagrammatic representation of a representative isosorbide useful in the molecular linker of the invention.
Figure 3C:
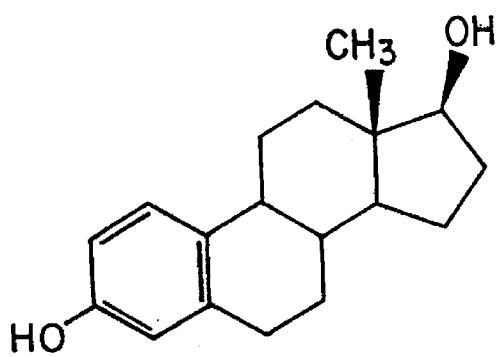
FIG. 3C is a diagrammatic representation of a steroid useful in the molecular linker of a finderon.
Figure 3D:
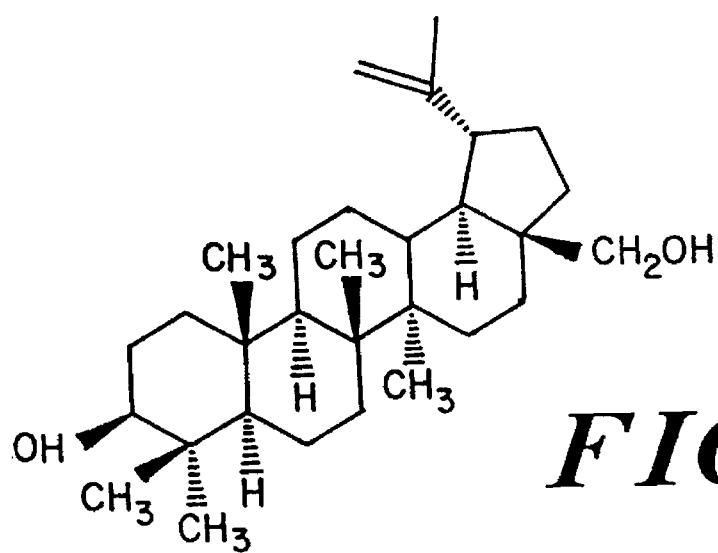
FIG. 3D is a diagrammatic representation of a representative lupene diol useful in the molecular linker of a finderon.

Other examples of cyclohexane diols that can be prepared and used in the linker include but are not limited to cis-1, 2-cyclohexanediol, cis- and trans-1,3 cyclohexanediol, and cis- and trans-1,4-cyclohexanediol. A representative useful isosorbide (or bis fused tetrahydrofuran) that can be prepared is 2-O-(4,4'-dimethoxytrityl)-5-O-[β-cyanoethoxy (N,N'-diisopropylamino)]phosphino-1,4:3,6-dianhydro-D-glucitol (FIG. 3B). A nonlimiting example of a useful lupene diol is 28-O-(4,4'-dimethoxytrityl)-3-O-(β-cyanoethoxy-N, N-diisopropylaminophophino) betulin (FIG. 3D). The molecular linker may be prepared from a number or combination of non-nucleotidic units by covalently linking the individual units together, one by one, in the same way that internucleotide linkages are formed, using well known H-phosphonate, phosphoramidite, or other methods performed manually or by an automated synthesizer.

For example, a multimolecular linker may be prepared via the silylphosphoramidite procedure outlined by Ma (*Biochemistry* (1993) 32:1751–1758) using nucleotide or linker molecule-bound control pore glass solid phase supports. For finderons containing at least one ribonucleoside, the deprotection and purification protocol of Ogilvie (*Meth. Mol. Biol.*(1993) 26:81–114) can be used. To prepare finderons not containing ribonucleotides or ribonucleotide analogs, the standard deprotection and the purification methods can be used (see, e.g., Atkinson et al. in *Oligonucleotide Synthesis: A practical approach.* (Gait, ed. ) IRL Press, Ltd. (Oxford) 1984, pp. 35–81) . However, in some finderons one non-nucleotidic unit is sufficient as a linker, as for example when the unit is a lupene diol.

The molecular linker is covalently attached at one end to the first nucleotidic flanking region, and at its other end, to the second nucleotidic flanking region. Each flanking region is composed of at least four, and commonly 6 to 20 contiguous, covalently-linked nucleotides and/or nucleotide analogs. These flanking regions contain nucleotide sequences which are complementary to, and hybridizable with specific target sequences on the RNA substrate to be cleaved. The target sequences complementary to the flanking regions may be contiguous or separated by one or several nucleotides, depending on the position of the cleavage site. Alternatively, the molecular linker and its flanking regions may be a component of an antisense oligonucleotide useful for other than ribozyme-type molecules.

Flanking regions of the finderons or antisense oligonucleotides of the invention are composed of deoxyribonucleotides, analogs of deoxyribonucleotides, ribonucleotides, analogs of ribonucleotides, or a combination thereof, with the 5' end of one nucleotide or nucleotide analog and the 3' end of another nucleotide or nucleotide analog being covalently linked. These flanking regions are at least four nucleotides in length, but are preferably six to fifty nucleotides long, with flanking regions of six to fifteen nucleotides being the most common.

These flanking regions can be prepared by the art-recognized methods such as phosphoramidate or H-phosphonate chemistry which can be carried out manually or by an automated synthesizer using standard H-phosphonate chemistry as described in U.S. Pat. No. 5,149,789, or using standard phosphoramidite chemistry (see, e.g., Beaucage (1993 ) *Meth. Mol. Biol.* 20:33–61); Damha et al. (in *Protocols for Oligonucleotides and Analogs; Synthesis and Properties* (Agrawal, ed.) (1993) Humana Press, Totowa, N.J., pp. 81–114); Goodchild (*Bioconjugate Chem.* (1990) 1:165–187).

The flanking regions may also be modified in a number of ways for protection against nuclease digestion, without compromising the ability of the finderon or antisense oligonucleotide to hybridize to target RNAs. For example, the nucleotides of the flanking regions may be covalently linked by other than phosphodiester internucleotide linkages between the 5' end of one nucleotide and the 3' end of another nucleotide, in which the 5' nucleotide phosphate has been replaced with any number of chemical groups. Examples of such chemical groups include alkylphosphonates, phosphorothioates, phosphorodithioates, alkylphosphonothioates, phosphoramidates, carbamates, acetamidates, carboxymethyl esters, carbonates, and phosphate triesters.

Other modifications include those which are internal or at the end(s) of the flanking region(s) and include additions to the internucleoside phosphate linkages, such as cholesteryl or diamine compounds with varying numbers of carbon residues between the amino groups, and terminal ribose, deoxyribose, and phosphate modifications. Examples of such modified flanking regions include nucleotide sequences having a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position). Other modified nucleotide sequences are capped with a nuclease resistance-conferring bulky substituent or self-hybridized region at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

The preparation of these modified oligonucleotides making up the flanking region is well known in the art (reviewed in Agrawal et al. (1992) Tren Biotechnol. 10:152–158; and Goodchild (1990) Biocougate Chem. 2:165–187). For example, nucleotides can be covalently linked using art-recognized techniques such as phosphoramidite, H-phosphonate chemistry, or methylphosphonamidite chemistry (see, e.g., Uhlmann et al. (1990) Chem. Rev. 90:543–584; Agrawal et al. (1987) Tetrahedron. Lett. 28: (31) :3539–3542); Caruthers et al. (1987) Meth. Enzymol. 154:287–313; U.S. Pat. No. 5,149,798). Oligomeric phosphorothioate analogs can be prepared using methods well known in the field (see, e.g., Zon in Protocols for Oligonucleotides and Analogs (Agrawal, ed.) Humana Press, Totowa, N.J.(1994) vol. 20, pp. 165–189).

The 3' terminus of the first flanking region and the 5' terminus of the second flanking region are covalently attached to the molecular linker by any of the methods described above. In some finderons, the second flanking region comprising at least one ribonucleotide, such as adenine, at its 5' terminus which is covalently linked to the linker. The second flanking region is covalently attached to the linker via its 5' terminus of the flanking region.

The structural characteristics of some finderons of the invention illustrated schematically in FIG. 2 are summarized below in TABLE 1. "Flanking Region" refers to the number of nucleotides in each of the first and second flanking regions, and "linker size" refers to the number of non-nucleotidic units in the linker.

TABLE 1

| Finderon | Flanking Region (nucleotides) | Linker Size (units) | SEQ ID NO: |
| --- | --- | --- | --- |
| TLI-77A | 10 | 4 | 1 |
| TLI-88A | 10 | 8 | 2 |
| TLI-95A | 10 | 12 | 3 |
| TLI-114A | 6 | 4 | 4 |
| TLI-116A | 6 | 8 | 5 |
| TLI-118A | 6 | 12 | 6 |
| TLI-122A | 4 | 1 | 7 |
| TLI-124A | 4 | 4 | 8 |
| TLI-126A | 4 | 6 | 9 |
| TLI-4A | 15 | 4 | 10 |
| TLI-6A | 15 | 8 | 11 |
| TLI-8A | 15 | 12 | 12 |

Using the methods described herein, finderons TL1–77A, (SEQ ID NO:1), TL1–88A (SEQ ID NO:2), TL1–95A (SEQ ID NO:3), TL1–114A (SEQ ID NO:4), TL1–116A (SEQ ID NO:5), and TL1–118A (SEQ ID NO:6) were synthesized and tested for their nucleolytic activity using a single-stranded substrate RNA as follows.

The experiments were conducted in parallel at pH 8, 9, and 10 in 50 mM Tris and a buffer containing magnesium chloride. Magnesium is believed to stabilize ribozyme-substrate RNA complexes and is involved in the cleavage reaction, itself. RZMZ-1 (SEQ ID NO:13), a ribozyme with known catalytic activity, was used as a positive control, and substrate RNA (SEQ ID NO:15) in the presence of magnesium was used as a negative control. Based on concentrations of stock solutions determined by UV analysis, samples of finderons TL1–77A, TL1–88A, and TL1–95A were aliquoted into tubes and evaporated. Then, substrate RNA radiolabelled internally with [$\alpha$-$^{32}$P]ATP was taken up in a magnesium-containing buffer and added to the various finderon samples. The reaction mixtures were incubated at 37° C. for one hour and then subjected to PAGE. The cleavage products in the gels were then analyzed by autoradiography.

Figure 6:
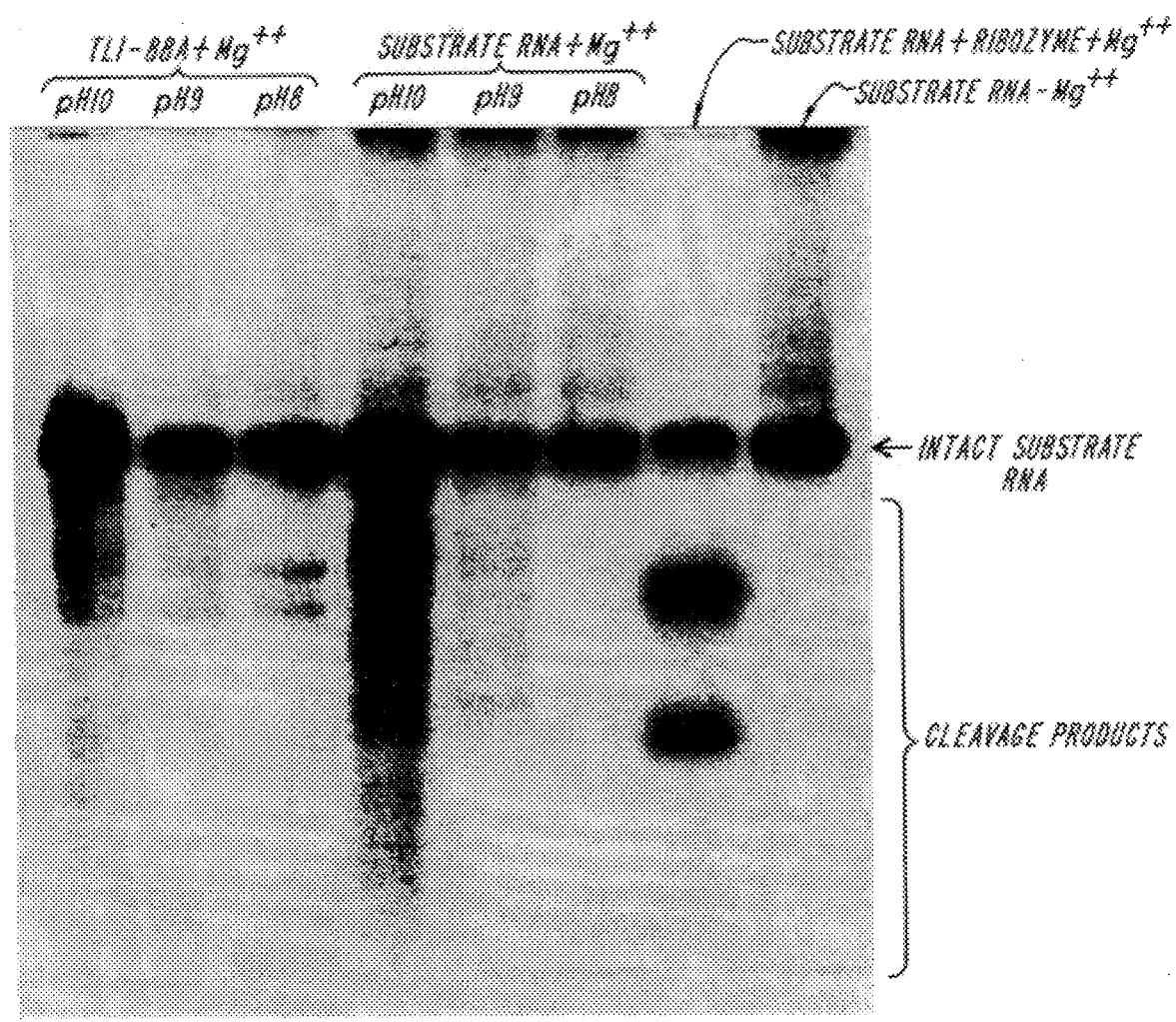
FIG. 6 is an autoradiogram of a polyacrylamide gel through which were run the cleavage products of finderon TL1-88A-treated substrate RNA at pH's 8–10 and control ribozyme-treated or untreated substrate RNA (control)

The results of representative assays are shown in FIG. 6. In this gel the substrate RNA samples that had been incubated with the finderons of the invention had been partially broken down into lower molecular weight, faster migrating cleavage products. These results demonstrate that the finderons have endonucleolytic activity at pHs 9 and 10.

Thus, finderons according to the invention are useful as RNA-specific restriction endonucleases, and as such, in combination with RNA ligases, allow for the preparation of recombinant RNA molecules.

Figure 5:
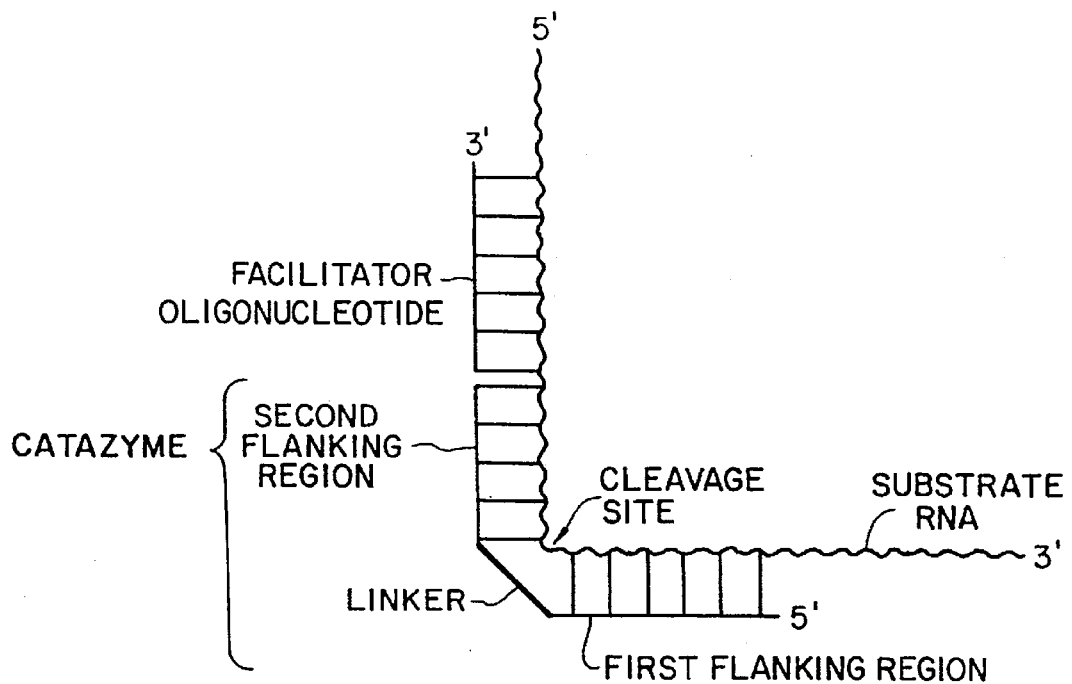
FIG. 5 is a schematic representation of the ternary finderon-substrate RNA facilitator (F1) oligonucleotide complex.

The cleavage abilities of a finderon may be enhanced by introducing a facilitator oligonucleotide into the system which hybridizes adjacent to the finderon (see WO 93/15194). Such a facilitator oligonucleotide may be selected to bind to a sequence contiguous with the substrate RNA sequence to which a flanking region binds at the 5' or the 3' side of the finderon. The catalytic complex formed by the substrate RNA, finderon, and facilitator oligonucleotide is depicted in FIG. 5. In some situations, a may be employed, where one facilitator is hybridized to the substrate RNA directly adjacent the nucleotide sequence hybridized to the first (3') flanking sequence of the finderon, and the other facilitator is hybridized to the substrate RNA directly adjacent the nucleotide sequence hybridized to the second (5') flanking sequence of the finderon. Alternatively, a plurality of facilitators may be employed to enhance finderon activity. For example, in a system employing three facilitators, two facilitators can bind contiguously to the RNA substrate sequence complementary to first (3') flanking sequence, while a single additional facilitator can bind contiguously to the RNA substrate sequence complementary to the second (5') flanking region. A variety of other combinations are possible.

In addition, facilitator oligonucleotides may have a nucleotide sequence complementary to regions of the RNA substrate that are not immediately contiguous with the substrate sequences complementary to the finderon flanking sequences of the desired finderon. For example, the facilitator may be synthesized such that, when the finderon and facilitator oligonucleotide are bound to the substrate RNA, a small gap of from one to about five oligonucleotides exists between the finderon and the facilitator oligonucleotide. Usually, the gap between the facilitator and the finderon will be between 0 (zero) and 2 nucleotides. Most often, there will be no nucleotide gap between the facilitator and the finderon.

The facilitator oligonucleotides useful in the present invention typically have between about 5 and 50 nucleotides. More preferred facilitator oligonucleotides comprise between about 5 and 15 deoxyribonucleotides. Particularly preferred facilitators according to the invention comprise about 13 nucleotides. Selection of a facilitator of a specific length is related to the length of the finderon flanking sequences. In addition, some facilitator deoxynucleotides may have a sequence of nucleotides, a portion of which is complementary to the RNA substrate sequence, and a portion of which that is not complementary to the substrate RNA sequence.

Facilitator oligonucleotides can be synthesized on automated DNA synthesizers or manually from DNA templates. They may be synthesized and subsequently modified to include moieties which will influence the rate of substrate cleavage by the finderon, increase uptake by cells, or increase resistance to degradation. For example, by increasing the number of bases of the substrate RNA bound near the cleavage site, facilitators permit use of faster acting finderons with shorter flanking sequences. In viral applications, facilitators might be of dual benefit in also directing cleavage of the viral RNA by endogenous ribonuclease H.

To determine the effect of the presence of a facilitator molecule and of reduced flanking sequence length on finderon activity, various finderons (TL1–114A (SEQ ID NO:4); TL1–116A (SEQ ID NO:5), and TL1–118A (SEQ ID NO:6), each with only six nucleotides in each flanking region, were incubated with substrate RNA (S2) (SEQ ID NO:15) and magnesium, or with substrate RNA and facilitator oligonucleotide in the presence of magnesium, at 37° C. The control ribozyme R5 (SEQ ID NO:16) was treated in the identical fashion. Aliquots were removed from the reaction mixtures tubes after 10 minutes to serve as finderon unincubated controls. After one hour, the reaction mixtures were placed on ice. An aliquot of an RNA substrate + facilitator stock solution also was taken as an unincubated RNA control. The resulting cleavage products were analyzed by polyacrylamide gel electrophoresis (PAGE).

Figure 7:
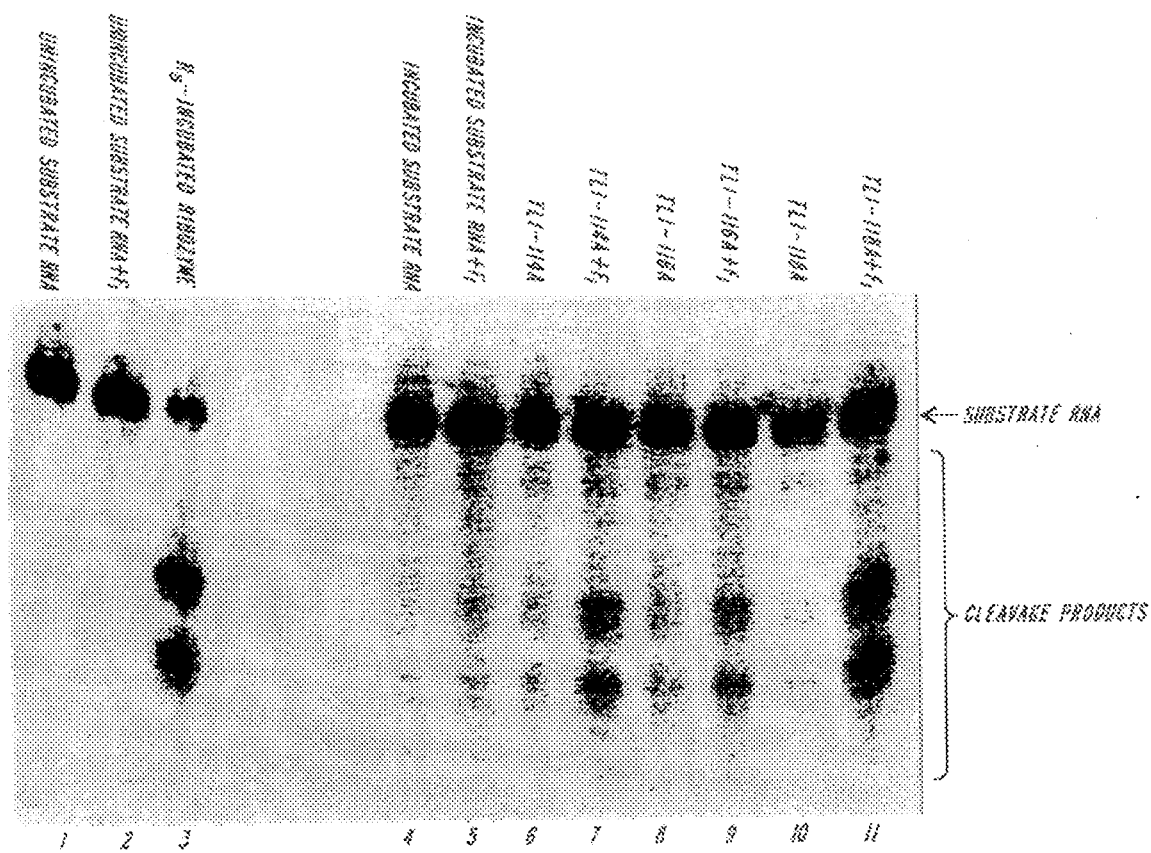
FIG. 7 is an autoradiogram of a polyacrylamide gel through which were run the cleavage products of finderon TL1-114A-, TL1-116-A-, or TL1-118A-treated substrate RNA at 45° C. in the presence or absence of facilitator oligonucleotide, and ribozyme-treated or untreated substrate RNA in the presence or absence of facilitator oligonucleotide at 37° C. (controls)

The results, shown in FIG. 7, demonstrate that substrate RNA samples that had been incubated with a finderon of the invention had been partially broken down into lower molecular weight, faster migrating cleavage products by specific cleavage the same site as at the control ribozyme. Greater cleavage occurred when a facilitator oligonucleotide was added to the incubation mixture (lanes 6, 9, and 11), further indicating the ability of the finderons of the invention to cleave RNA. Finderons with 4-, 8-, and 12-unit linkers have similar catalytic activities in the absence of the facilitator. However, in the presence of facilitator, finderons with the 12-unit linker had more activity than finderons with either the 4- or 8-unit linker.

The finderons of the invention can be provided for any method of use in the form of a kit including a container of finderons, of mixtures of different finderons, or of finderons and facilitator oligonucleotide, with or without a container of facilitator oligonucleotide(s) alone. The amount of finderon or of finderon and facilitator oligonucleotide in the container may be sufficient for one therapeutic dose or assay. Alternatively, the amounts of the kit constituents may be concentrated such that only small aliquots need be sampled at one time from the container when used, for example, to cleave RNA molecules in vitro.

The present invention also provides therapeutic formulations containing a finderon, or a finderon and facilitator oligonucleotide(s) useful for treatment. These therapeutic formulations must be administered to individuals in a manner capable of delivering the finderon or antisense oligonucleotide initially into the body and subsequently into cells.

One mode of administration is via a therapeutic formulation which contains at least one finderon, as described above, along with a physiologically acceptable carrier. Some therapeutic formulations contain more than one type of finderon of the invention, and some include facilitator oligonucleotides.

As used herein, a "physiologically acceptable carrier" includes any and all solvents, dispersion media, coatings, antibacterial and antifungal agents, isotonic and absorption-delaying agents, and agents which improve oligonucleotide uptake, and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

The therapeutic formulations of the invention may be administered parenterally, orally, by inhalation of spray, or rectally in dosage unit formulations containing conventional non-toxic pharmaceutically acceptable carriers, adjuvants and vehicles. The term "parenteral" as used herein includes subcutaneous injections, intravenous, intramuscular, intrasternal injection or infusion techniques.

The amount of active composition that may be combined with the carrier materials to produce a single dosage form will vary depending upon the host treated and the particular mode of administration. It will be understood that the specific dose level for any particular patient will depend upon a variety of factors including the activity of the specific composition employed, the age, body weight, general health, sex, diet, time of administration, route of administration, severity of the particular disease undergoing therapy.

The finderons of the invention, themselves, or in a therapeutic formulation may be administered for any purpose known to those with skill in the art that a ribozyme or antisense oligonucleotide may be used. For example, cells infected with a virus may be treated with a finderon having flanking sequences complementary to nucleotide sequences of a particular mRNA corresponding to a viral gene to hinder the expression of that gene. Similarly, finderons may be administered to stop the expression of cancer-related genes, or of any gene which is being overexpressed.

The following examples illustrate the preferred modes of making and practicing the present invention, but are not meant to limit the scope of the invention since alternative methods may be utilized to obtain similar results.

EXAMPLES

1. Preparation of Non-Nucleotidic Linker

In order to prepare a trans-1-O-(4,4'-dimethoxytrityl)-2-O-[β-cyanoethoxy-(N,N-diisopropylamino)]phosphino-1,2-cyclohexanediol-containing linker, a precursor form of the unit, trans-1-O-dimethoxytrityl-1,2-cyclohexanediol is needed. This precursor is prepared as follows:

1.16 g (10 mmol) of trans-1,2-cyclohexanediol was dissolved in 50 ml of anhydrous pyridine. This solution was evaporated to dryness and the procedure was repeated twice to remove any water present. The flask was then sealed and flushed with argon. Next, a solution was made by dissolving 3.4 g (10.1 mmol) of dimethoxytrityl chloride and 20 mg of dimethylaminopyridine in 50 ml of anhydrous pyridine. This solution was added to the first mixture, via syringe, dropwise over 30 minutes. This reaction mixture was then stirred at room temperature for 18 hours.

An aliquot of the solution was analyzed by thin layer chromatography (TLC) in hexane:ethyl acetate:triethylamine (50:20:1), yielding a spot corresponding to the desired product and faint spots corresponding to dialkylated product and dimethoxytritanol. The solvent was removed in vacuo and the residue taken up in 125 ml of dichloromethane. This was washed with 5% sodium bicarbonate and twice with brine. The solvent was removed and the resulting gum taken up in hexanes:ethyl acetate:triethylamine and applied to a silica gel column containing the same solvent. Fractions containing the desired product were combined and evaporated to give 1.0 g (2.38 mmol) 25% yield of product.

Material prepared by this method was used in the next step by dissolving 3.72 g (8.9 mmol) in 40 ml of anhydrous THF, and then evaporating it to dryness. The procedure was repeated twice. Next, the residue was taken up in 40 ml of THF, to which was added 6.2 ml of diisopropylethylamine (35.4 mmol). The flask was sealed and flushed with argon. Then, 4.21 g (17.8 mmol) of [β-cyanoethyoxy (N,N-diisopropylamino)] chlorophosphine in 25 ml of dry THF was added dropwise with stirring at room temperature, over 30 minutes. A white precipitate formed. 45 minutes after the final addition, TLC in hexanes: ethyl acetate: triethylamine, 50:20:1, showed the reaction to be complete. 1 ml of water was added and the reaction mixture stirred for 15 minutes. Solvent was evaporated and the residue taken up in 250 m of ethyl acetate. The organic layer was washed once with 75 ml of 5% sodium bicarbonate and once with 75 ml of brine. It was then dried over sodium sulfate, filtered, and evaporated to a small volume. The residue was applied to a silica gel column and the desired product eluted in hexanes:ethylacetate:triethylamine, 50:10:1. The fractions containing the desired product were pooled and evaporated to give 3.68 g (5.94 mmol) 67% yield of desired product.

2. Chemical Synthesis of Finderons

The nucleotidic flanking regions containing unmodified (phosphodiester-linked) deoxyribonucleotides, ribonucleotides, or both, were synthesized on an automated DNA synthesizer (Applied BioSystems, Foster City, Calif.) on a 1.0 μmole scale using standard H-phosphonate chemistry as described in U.S. Pat. No. 5,149,789, or using standard phosphoramidite chemistry as described by Beaucage (*Meth. Mol. Biol.* (1993) 20:33–61) or Uhlmann et al. (*Chem. Rev.* (1990) 90:534–583). Flanking regions with at least one nonphosphodiester internucleotide linkage including a phosphoramidite, methylphosphonate, and/or a 2'-O-methyl linkage at preselected positions were prepared using the procedures described in Agrawal and Goodchild (*Tetrahedron Lett.* (1987) 28:3539–3542); Agrawal et al. (*Proc. Natl. Acad. Sci.(USA)* (1988) 85:7079–7083); and/or Uhlmann et al. (*Chem. Rev.* (1990) 90:534–583). Flanking regions having at least one phosphorodithioate, carbamate, phosphate ester, 2'-O-methyl, alkylphosphonate, phosphoramidate, alkylphosphonothioate, carbonate, acetamidate, and/or carboxymethyl ester were prepared as described in Uhlmann et al. (*Chem. Rev.* (1990) 90:534–583).

Non-nucleotide phosphoramidites were incorporated into oligonucleotides using the same standard protocols as for nucleotides.

The product was cleaved from the support and deprotected by heating in 1 ml of concentrated aqueous ammonia= ethanol (3:1 v/v) in a sealed tube at 55° C. for 17 hours. Following centrifugation, the support was washed twice with 400 μl of water, and the combined supernatant and washings were divided in half and placed in separate tubes and evaporated to dryness. One tube was stored at −20° C. for later use; the other was treated with 400 μl of tetra-N-butylammonium fluoride (TBAF) 1.0M in THF (Aldrich Chemical Co., Milwaukee, Wisc.) for 16 hours at room temperature.

3. Purification of Finderons

To the oligonucleotide sample was added 400 μl of 50 mM Tris, pH 8 and 800 μl of 95% formamide containing 0.05% Orange G dye (Sigma, St. Louis, Mo.). The sample was then loaded onto a 15% polyacrylamide gel containing 8M urea. Electrophoresis was carried out at 25 watts constant power until the dye reached the bottom of the gel. The desired band was identified by shadowing with a UV lamp against a fluorescent background. This band was cut out of the gel, crushed with a pestle, and extracted with 12 ml of 0.5M ammonium acetate for 12 hours. The mixture was centrifuged and the supernatant removed. The pellet was reextracted with 4 ml 0.5M ammonium acetate for 2 hours. The mixture was centrifuged and the combined supernatants passed through a Sep-Pak cartridge (Waters, Marlborough, Mass.) at a rate of 2 ml per minute. The cartridge was washed with water and the finderon eluted with 4 ml 50% aqueous acetonitrile at 2 ml per minute. The eluate was evaporated and the residue taken up in 200 μl of 0.3M NaCl. Next, 600 μl of absolute ethanol was added and the mixture stored at −20° C. for 16 hours. The mixture was centrifuged and the supernatant decanted. The pellet was redissolved in 200 μl of 0.1M NaCl and precipitated with 600 μl of absolute ethanol. The suspension was placed on dry ice for 30 minutes and centrifuged. The supernatant was removed and the pellet dissolved in 400 μl of water and stored at −20° C. until used.

4. Preparation of Facilitator Oligonucleotide

Facilitator oligonucleotides which contain unmodified (phosphodiester-linked) deoxyribonucleotides were synthesized on an automated DNA synthesizer (Applied BioSystems, Foster City, Calif.) as described in EXAMPLE 2 above.

5. Assay for RNA Cleavage Activity of Finderons

Substrate RNA radiolabelled internally using [α-$^{32}$P]ATP (Amersham, Arlington Heights, Ill.) was prepared as described by Goodchild et al. (*Arch. Biochem. Biophys.* (1991) 284:386–391) using T7 RNA polymerase (New England Biolabs, Beverly, Mass.) and a chemically synthesized single stranded template with a double stranded promoter (Milligan et al. (1987) *Nucleic Acids Res.* 15:8783–8798).

The experiments were conducted simultaneously at pH 8, 9, and 10 in 50 mM Tris buffer containing 20 mM magnesium chloride. The final finderon concentration in all cases was 50 μM and that of substrate was 4 nM. Final reaction volumes were 5 μl. An active ribozyme (FIG. 1) was used as a positive control, and substrate RNA alone in 20 mM magnesium chloride, 50 mM Tris was used as a negative control. Based on concentrations of stock solutions determined by UV analysis, desired amounts of finderon samples TL1-77A, TL1-88A, and TL1-95A were evaporated. The substrate was taken up in Tris-magnesium buffer and added to the evaporated finderon samples. The mixtures were then incubated at 37° C. for one hour. Next, 5 μl 95% formamide dye containing 0.05% Orange G dye was added and the reaction mixtures loaded directly onto a preheated (45° C. ), 15% polyacrylamide gel was containing 8M urea. The gel is analyzed using a phosphorimager (Molecular Dynamics, Sunnyvale, Calif.) and by autoradiography.

6. The Effects of Reduced Flanking Sequence Length and Facilitator Presence on Finderon Cleavage activity The following procedure was used to examine the effects of reduced flanking sequence length and facilitator presence on the cleavage activity of finderons TL1–114A (SEQ ID NO:4), TL1–116A (SEQ ID NO:5), and TL1–118A (SEQ ID NO:6). Based on concentrations of stock solutions of finderons obtained on work up, 25 picomoles of each of the finderons were taken up and evaporated. Substrate RNA (S2) (SEQ ID NO:15) was prepared according to the procedure of Goodchild et al. (*Arch. Biochem. Biophys.* (1991) 284:386–391) or of Milligan et al. (*Nucleic Acids Res.* (1987) 15:8783–8798). Two stock solutions of substrate were prepared; one containing 0.5 µM RNA substrate and the other containing 0.5 µM substrate plus 1.0 µM facilitator oligonucleotide, F1 (SEQ ID NO:14). Both stock solutions contained 50 mM Tris, pH 9, and 20 mM magnesium chloride. All ribozyme samples contained 20 mM magnesium chloride and 50 mM Tris, pH 9. Control ribozyme R5 (SEQ ID NO:16) was treated in the identical fashion. Final reaction volumes were 10 µl.

All tubes were heated to 37° C. for 10 minutes. Five microliter aliquots were removed from the substrate and substrate + facilitator. Five microliters of 95% formamide dye containing 0.05% Orange G dye were added, and these mixtures, which served as unincubated controls, were placed on ice. Next, 5 µl of substrate stock was added to each of the tubes containing finderon or ribozyme control R5 (SEQ ID NO:16). Also, 5 µl were taken as an incubated control. Then, 5 µl of substrate + facilitator were taken as an unincubated RNA control, and 5 µl added to duplicate tubes containing the finderons. All tubes except those containing the unincubated controls were heated at 37° C. for one hour.

7. Electrophoretic Analysis of Cleavage Products

20 µl of orange formamide dye were added to each reaction tube described in EXAMPLE 5 above, and the contents loaded onto a 15% polyacrylamide gel containing 8M urea, preheated to 45° C. Electrophoresis was carried out at 25 watts constant power until the dye was off the bottom of the gel. The results from phosphor-imaging the gel are shown in FIGS. 6 and 7.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. A method of site-specifically cleaving a single-stranded, RNA-containing substrate, comprising the step of contacting the RNA-containing substrate with a finderon for a time sufficient for the finderon to hybridize to and cleave the RNA containing substrate, the finderon comprising:

(a) a first flanking region comprising from four to fifteen contiguous, covalently-linked nucleotides, at least a portion of the first flanking region being complementary to a first target region located at a 3' position of a cleavage site on a substrate RNA molecule;

(b) a second flanking region comprising from four to fifteen contiguous, covalently-linked nucleotides, at least a portion of the second flanking region being complementary to a second target region located at a 5' position of the cleavage site; and (c) a rigid linker covalently bound to a 3' terminus of the first flanking region and to a 5' terminus of the second flanking region, the linker comprising from one to twelve non-nucleotidic units maintaining the cleavage site in a trigonal bipyramidal transition state conformation, and wherein the non-nucleotidic unit is selected from the group consisting of a cyclohexane diol, asteroid, a lupene diol, an isosorbide, and combinations thereof and a linear distance of about 15 to 30 Angstroms is established between the first and second flanking regions.

2. The method of claim 1 wherein the RNA-containing substrate is further contacted with a facilitator oligonucleotide at the time it is contacted with the finderon.

3. The method of claim 1 wherein the linker comprises at least two non-nucleotidic molecules covalently-linked to each other and to the first and second flanking regions via a linkage selected from the group consisting of a phosphodiester, an alkylphosphonates, a phosphate ester, a phosphorothioate, a phosphorodithioate, an alkylphosphonothioate, a phosphoramidate, a carbamate, a carbonate, an acetamidate, and a carboxymethyl ester, and combinations thereof.

4. The method of claim 1 wherein the linker comprises at least one cyclohexane diol unit.

5. The method of claim 4 wherein the linker comprises at least four contiguous covalently linked cyclohexane diol units.

6. The method of claim 5 wherein the linker contains 3–5 cyclohexane diol units.

7. The method of claim 4 wherein the cyclohexane diol unit is selected from the group consisting of trans-1,2-cyclohexane diol, cis-1,2-cyclohexane diol, trans-1,3-cyclohexane diol, cis-1,3-cyclohexane diol, trans-1,4-cyclohexane diol, cis-1,4-cyclohexane diol, and combinations thereof.

8. The method of claim 1 wherein the nucleotides comprising the first and second flanking regions are selected from the group consisting of deoxyribonucleotides, analogs of debxyribonucleotides, ribonucleotides, analogs of ribonucleotides, and combinations thereof.

9. The method of claim 8 wherein the ribonucleotide or deoxyribonucleotide analogs in the first and second flanking regions are selected from the group consisting of an alkylphosphonate, a phosphorothioate, a phosphorodithioate, an alkylphosphonothioate, a phosphoramidate, a phosphate ester, a carbamate, a carbonate, an acetamidate, a carboxymethyl ester, and combinations thereof.

10. The method of claim 8 wherein the ribonucleotide analogs in the first and second flanking regions are 2'-O-methyl ribonucleotide analogs.

11. The method of claim 1 wherein at least one nucleotide in the first flanking region is a ribonucleotide.

12. The method of claim 11 wherein the ribonucleotide in the first flanking region is adenosine.

13. The method of claim 11 wherein the first flanking region and the second flanking region each comprise at least 6 to 15 covalently linked nucleotides.

14. The method of claim 1 wherein the nucleotides in the first and second flanking regions are covalently linked via an internucleotide linkage selected from the group consisting of a phosphodiester, an alkylphosphonate, a phosphorothioate, a phosphorodithioate, an alkylphosphonothioate, a phosphoramidate, a phosphate ester, a carbamate, a carbonate, an acetamidate, a carboxymethyl ester, and combinations thereof.

15. The method of claim 1 wherein the fideron, when hybridized to the substrate RNA, establishes a linear conformation in the substrate RNA at the cleavage site wherein a zeta angle of about 180° exists between a 3' oxygen of the cleavage site and a phosphorus atom to which the oxygen is covalently bound.

* * * * *

UNITED STATES PATENT AND TRADEMARK OFFICE
CERTIFICATE OF CORRECTION

PATENT NO. : 5,627,055
DATED : May 6, 1997
INVENTOR(S) : Goodchild et al.

It is certified that error appears in the above-indentified patent and that said Letters Patent is hereby corrected as shown below:

In claim 1, line 45, after "diol,", "asteroid" should be changed to --a steroid--.

Signed and Sealed this

Twenty-first Day of October 1997

BRUCE LEHMAN

*Attest:*

*Attesting Officer*     Commissioner of Patents and Trademarks